United States Patent [19]

Maryanoff et al.

[11] Patent Number: 4,591,601
[45] Date of Patent: May 27, 1986

[54] ANTICONVULSANT DIOXOLANE METHANE SULFAMATES

[75] Inventors: Bruce E. Maryanoff, New Hope; Samuel O. Nortey, Lamott, both of Pa.

[73] Assignee: McNeilab, Inc., Fort Washington, Pa.

[21] Appl. No.: 722,869

[22] Filed: Apr. 12, 1985

[51] Int. Cl.⁴ .............. A61K 31/335; C07D 319/00; C07D 317/00

[52] U.S. Cl. ................... 514/462; 514/467; 549/333; 549/451; 549/453

[58] Field of Search .......... 549/453, 333, 451; 514/462, 467

[56] References Cited

U.S. PATENT DOCUMENTS

| | | | |
|---|---|---|---|
| 3,058,981 | 10/1962 | Avakian et al. | 260/247.2 |
| 3,246,012 | 4/1966 | Feit | 549/453 |
| 3,948,953 | 4/1976 | McCoy | 549/453 |
| 4,075,351 | 2/1978 | Hirsch | 424/303 |

FOREIGN PATENT DOCUMENTS

| | | | |
|---|---|---|---|
| 0197258 | 12/1982 | Japan | 549/453 |
| 976534 | 11/1964 | United Kingdom | 549/453 |

OTHER PUBLICATIONS

N. K. Kochetkov et al. in Zhurnal Obshchei Khimii, vol. 41, No. 8, pp. 1874–1878, (1971).

N. K. Kochetkov et al. in Journal of General Chemistry of the USSR 42 (12) 2755–2757 (1972).

N. K. Kochetkov et al. in Journal of General Chemistry of the USSR 44 (4) 871–875 (1974).

N. K. Kochetkov et al. in Doklady Akademii Nauk SSSR, vol. 216, No. 1, pp. 97–100, (1974).

Tetrahedron Letters No. 36, pp. 3365–3368, Pergamon Press Ltd. (1978) by T. Tsuchiya.

J. Med. Chem. 1981, 24, 901–903, A. F. Hirsch.

*Primary Examiner*—Ethel G. Love
*Attorney, Agent, or Firm*—David J. Levy

[57] ABSTRACT

Sulfamates of the following formula (I):

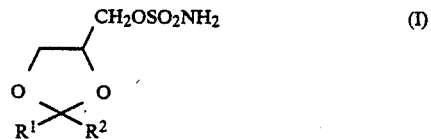

wherein $R^1$ and $R^2$ are as herein defined have been found to exhibit anticonvulsant activity and are thus useful in the treatment of conditions such as epilepsy. Further, pharmaceutical compositions containing a compound of formula (I) as well as methods for their use and intermediates form part of the present invention.

21 Claims, No Drawings

ANTICONVULSANT DIOXOLANE METHANE SULFAMATES

Sulfamates of various structures, including those derived from monosaccharides are described in references such as N. K. Kochetkov et al in Zhurnal Obshchei Kimii, Vol. 41, No. 8, 1866 to 1871 (1971), Vol. 42, No. 12, 2755 to 2757 (1972) and Vol. 44, No. 4, 871 to 875 (1974) and in Doklady Akademii Nauk SSR, Vol. 216, No. 1, 97 to 100 (1974); T. Tsuchiya et al, in Tetrahedron Letters, No. 36, 3365 to 3368 (1978); and A. F. Hirsch in Journal of Medicinal Chemistry, 24, 901 to 903 (1981) and U.S. Pat. No. 4,075,351. Also known are carbamates, including dioxolane carbamates such as dioxamate as described in U.S. Pat. No. 3,058,981.

SUMMARY OF THE INVENTION

It has been found that sulfamates of the following formula (I):

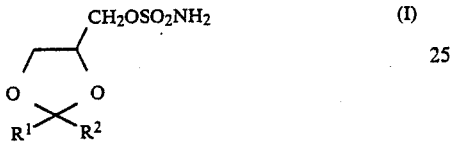

wherein $R^1$ and $R^2$ are as hereinafter defined, possess anticonvulsant acitivity in mammals and are thus useful in treating disease states such as epilepsy. Also, because of activity in the inhibition of the enzyme carbonic anhydrase, such compounds are useful in treating glaucoma. Also part of the present invention are pharmaceutical compositions containing one or more sulfamates of formula (I) as well as methods for the treatment e.g., prevention, of convulsions using such compositions.

DETAILED DESCRIPTION OF THE INVENTION

The sulfamates of the invention are of the following formula (I):

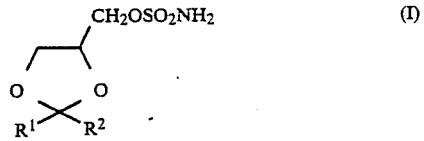

wherein
$R^1$ and $R^2$ are alkyl or taken together are joined to form a cycloalkyl ring.

$R^1$ and $R^2$ in particular are alkyl of about 1 to 10 carbons, such as methyl, ethyl, iso-propyl, tert-butyl, n-hexyl and n-nonyl. Alkyl throughout this specification includes straight and branched chain alkyl. $R^1$ and $R^2$ may also be taken together in particular, to join to form a 3 to 7 membered carbocyclic aliphatic ring, e.g. a cycloheptyl, cyclohexyl or cyclopentyl ring.

The compounds of formula (I) may be synthesized by the following methods:

(a) Reaction of an alcohol of the following formula (II):

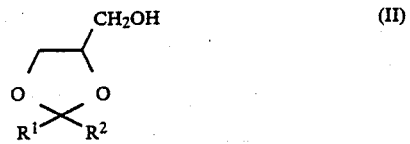

with a chlorosulfamate of the formula $ClSO_2NH_2$ in the presence of a base such as potassium t-butoxide or sodium hydride at a temperature of about $-20°$ to $25°$ C. and in a solvent such as toluene, THF or dimethylformamide.

(b) Reaction of an alcohol of the formula (II) above with sulfurylchloride of the formula $SO_2Cl_2$ in the presence of a base such as triethylamine or pyridine at a temperature of about $-40°$ to $25°$ C. in a solvent such as diethyl ether or methylene chloride to produce a chlorosulfate of the following formula (III):

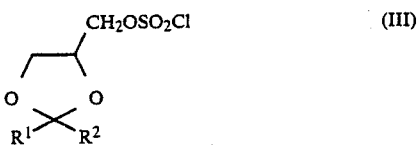

The chlorosulfate of the formula (III) may then be reacted with ammonia at a temperature of about $-40°$ to $25°$ C. in a solvent such as methylene chloride or acetonitrile to produce a compound of formula (I). The reaction conditions for process (b) are also described by T. Tsuchiya et al. in Tet. Letters, No. 36, pages 3365 to 3368 (1978).

(c) Reaction of the chlorosulfate (III) with a metal azide such as sodium azide in a solvent such as methylene chloride or acetonitrile yields as azidosulfate of the following formula (IV):

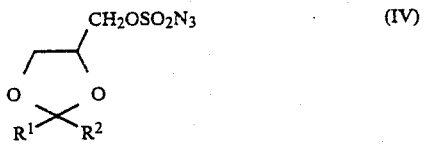

as described by M. Hedayatullah in Tet. Lett. p. 2455-2458 (1975). The azidosulfate is then reduced to a compound of formula (I) by catalytic hydrogenation, e.g. with a noble metal and $H_2$ or by heating with copper metal in a solvent such as methanol.

The starting materials of formula (II) may be obtained commercially or by techniques known to those skilled in the art of organic chemistry. For example, starting materials of formula (II) may be prepared by the condensation of glycerol with a ketone of the formula $R^1COR^2$ in the presence of p-toluene sulfonic acid.

The compounds of the invention include the various individual isomers as well as the racemates thereof, e.g., isomerism resulting from branching in the $R^1$ and $R^2$ groups and the various alpha and beta attachments, i.e., $R^1$ and $R^2$ below and above the plane of the drawing. Also included within the scope of the compounds of formula (I) of this invention are various hydrates and solvates.

The compounds of formula (I) are useful as anticonvulsant agents. The anticonvulsant activity of the subject compounds was determined using a standard "maximal electroshock test" (MES). In this test, activity is indicated by a block of the tonic extensor seizure caused by application of an electric shock to mice via corneal electrodes, as described by Swinyard et al in J. Pharmacol. Exptl. Therap. 106, 319 (1952). A more recent description of current anticonvulsant drug screening is given in Swinyard et al in Epilepsia 19, 409 (1978). Non-fasted male albino mice of the Swiss Webster strain (Royal-Hart Laboratories, New Hampton, N.Y.) weighing 18–24 grams were used in this test. Six to eight groups of ten mice each were used per $ED_{50}$ determination. The product of Example 1b was administered in aqueous solution while the compounds produced in Examples 2 and 3 were administered as suspensions prepared with Tween 80 and water. Testing was conducted at 30 minutes following intraperitoneal injection of the test compound. A group of ten mice injected with saline 10 ml/kg i.p. and tested 30 minutes later served as controls. $ED_{50}$'s were calculated using a computerized probit analysis procedure.

The anticonvulsant activity of compounds of this invention tested according to the Swinyard (1952) method is shown in the following Table I:

TABLE I

| Example | Compound | MES Test $ED_{50}$ (mg/kg, i.p.) |
|---|---|---|
| 1b. | $CH_2OSO_2NH_2$, $CH_3$, $CH_3$ (dioxolane) | 104.9 |
| 2 | $CH_2OSO_2NH_2$, $CH_3$, $n\text{-}C_9H_{19}$ (dioxolane) | 318.9 |
| 3 | $CH_2OSO_2NH_2$, cyclohexyl spiro-dioxolane | 168.6 |

For treating epilepsy, a compound of formula (I) may be employed at a daily dosage in the range of about 30 to 2000 mg, usually in 2 to 4 divided doses, for an average adult human. A unit dose would contain about 10 to 500 mg of the active ingredient.

In general, compounds of formula (I) may be used in treating epilepsy in a manner similar to that used for phenytoin. Medical aspects of the treatment of epilepsy are described by L. S. Goodman et al. in "The Pharmacological Basis of Therapeutics", 5th Ed. pages 201 to 226, Macmillan (1975).

Further, compounds of formula (I) are inhibitors of carbonic anhydrase, as determined by the methods described by S. J. Dodgson et al in the Proc. Natl. Acad. Sci., U.S., 77, pages 5562 to 5566 (1980) or by N. Itada et al in the Journal Biol. Chem., 252, pages 3881 to 3890 (1977) and as such, are useful in the treatment of glaucoma. The relationship between the treatment of glaucoma and carbonic anhydrase inhibition is described by A. Stein et al in the American Journal of Opthalmology, 95:222–228 (1983). For the treatment of glaucoma, a compound of formula (I) may be administered systemically, e.g. by oral or parenteral routes as described below, or topically in the eye in a mineral oil solution or suspension, or aqueous suspension. When used systemically, the compound would be administered in an amount of about 50 to 500 mg per day for an average adult human, while the topical dosage would be about 1 to 3 drops (per eye) of a solution of suspension containing about 1 to 5% by weight of a compound of formula (I) with the dosage being administered about 1 to 4 times per day.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The pharmaceutical compositions herein will contain, per dosage unit, e.g., tablet, capsule, powder, injection, teaspoonful, suppository and the like, from about 10 to about 500 mg of the active ingredient.

The foregoing compositions are particularly suitable for use in the treatment of epilepsy or the symptoms of epilepsy by a method comprising internally administering to a subject suffering from the symptoms of epilepsy compositions comprising an effective epilepsy inhibiting amount of a compound of formula (I).

Also part of the present invention are intermediates of the formulae (III) and (IV).

In the following Examples and throughout the specification the following abbreviations may be used: g (grams); ml (milliliters); min (minutes); hr (hours); mol (moles); cm (centimeters); v/v (volume to volume); i.p. (intraperitoneally); mg/kg (milligrams per kilogram of body weight); mp (melting point); TLC (thin layer chromatography); HPLC (high pressure liquid chromatography); NMR (nuclear magnetic resonance); IR (infrared); DMF (dimethylformamide); THF (tetrahydrofuran); and C, H, N, etc. (the chemical symbols for the elements).

EXAMPLE 1 a. Sulfamoyl Chloride

Sulfamoyl chloride is prepared by the method described by R. Appel and G. Berger in Chem. Ber., Vol. 91, page 1339-41 (1958) from chlorosulfonyl isocyanate (Aldrich) and formic acid.

b. (2,2-Dimethyl-1,3-dioxolan-4-yl)methyl sulfamic acid ester $R^1=R^2=CH_3$      Formula (I)

A mixture of 25 g (0.189 mole) of 2,2-dimethyl-1,3-dioxolane-4-methanol (Aldrich-"Solketal") in 150 ml of DMF was added dropwise to a suspension of sodium hydride (11 g. 50% in oil; 0.23 mole) in 150 ml of DMF at 0°-5° C. The suspension was stirred for 30 min. under argon after which sulfamoyl chloride (24 g; 0.21 mole) was added portionwise at 0°-5° C., keeping the pH of the solution above 7 (using triethylamine when necessary). The resultant solution was stirred for an additional 15 min., poured into ice and extracted twice with chloroform. The combined organic phases were washed once with water, dried over anhydrous sodium sulfate and concentrated in vacuo to a thin syrup which was purified by preparative HPLC with hexane/ethyl acetate (1:1, v/v) as the eluant to give 17.7 g (44%) of (2,2-dimethyl-1,3-dioxolan-4-yl)methyl sulfamic acid ester.

Elemental Analysis: Calculated for $C_6H_{13}NO_5S$: C, 34.12; H, 6.20; N, 6.63. Found: C, 34.15; H, 6.19; N, 6.51.

EXAMPLE 2

(2-Methyl-2-nonyl-1,3-dioxolan-4-yl)methyl sulfamic acid ester Hydrate compound with 2-undecanone (10:1:2)

$R^1=CH_3, R^2=n-C_9H_{19}$      Formula (I)

A solution of 2-methyl-2-nonyl-1,3-dioxolane-4-methanol (25 g, 0.102 mole) (prepared by the method described by S. Avakian and G. J. Martin in U.S. Pat. No. 3,058,981) in 50 ml of toluene was added dropwise to a suspension of sodium hydride (6.38 g, 50% in oil, 0.133 mole) in 150 ml of DMF at 0°-5° C. The suspension was stirred under argon for 30 min. Sulfamoyl chloride (15.3 g, 0.132 mole) was added portionwise at 0°-5° C. and the resultant solution was stirred for an additional 15 min., poured into ice and extracted with ethyl ether. The ether extract was washed once with water and then saturated brine, dried over anhydrous magnesium sulfate and concentrated to a thin syrup which was purified by preparative HPLC with hexane/ethyl acetate (4:1 v/v) as the eluant to give 12.48 g (39%) of the title compound, a waxy solid, mp=49°-51° C.

Elemental Analysis: Calculated for $C_{14}H_{29}NO_5S \cdot 0.1C_{11}H_{22}O \cdot 0.2H_2O$: C, 52.71; H, 9.26; N, 4.07; $H_2O$, 1.05. Found: C, 52.50; H, 9.15; N, 4.31; $H_2O$, 0.69.

EXAMPLE 3

(1,4-Dioxaspiro[4.5]dec-2-yl)methyl Sulfamic acid ester.

$R^1,R^2=-(CH_2)_5-$      Formula (I)

A mixture of glycerol (50 g, 0.54 mole), p-toluene sulfonic acid (1.5 gm) and cyclohexanone (52.92 g; 0.54 mole) in toluene (150 ml) was refluxed while water was being removed under a Dean-Stark trap. After 2 hr. the reaction mixture was cooled, washed with water and saturated brine, dried over anhydrous potassium carbonate and filtered. After filtration, the solution was concentrated to yield 64.6 gms (69%) of a light yellow syrup. 20 g (0.12 mol) of this syrup was added dropwise to a suspension of sodium hydride (7.24 g, 0.15 mol) in 150 ml of DMF at 0°-5° C. The resultant syrup was stirred for an additional 30 min under argon after which sulfamoyl chloride (23 g. 0.2 mole) was added portionwise at 0°-5° C. The resultant solution was stirred for 15 minutes, poured into ice and extracted with ethyl ether. The ether solution was washed with water and saturated brine, dried over anhydrous magnesium sulfate and concentrated to give a syrup which was purified by preparative HPLC with hexane/ethyl acetate (4:1 v/v) as the eluant to yield 11.5 g (38%) of pure (1,4-dioxaspiro[4.5]dec-2-yl)methyl sulfamic acid ester.

Elemental Analysis: Calculated for $C_9H_{17}NO_5S$: C, 43.02; H, 6.82; N, 5.57. Found: C, 42.89; H, 6.91; N, 5.29.

What is claimed is:

1. A sulfamate of the following formula (I):

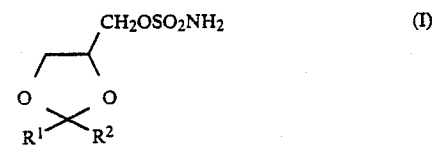

wherein $R^1$ and $R^2$ are alkyl or taken together are joined to form a cycloalkyl ring.

2. The sulfamate of claim 1, wherein $R^1$ and $R^2$ are independently alkyl of 1 to about 10 carbons.

3. The sulfamate of claim 2, wherein $R^1$ and $R^2$ are independently methyl, ethyl, iso-propyl, tert-butyl, n-hexyl or n-nonyl.

4. The sulfamate of claim 1, wherein $R^1$ and $R^2$ taken together are joined to form a 3 to 7 membered carbocyclic aliphatic ring.

5. The sulfamate of claim 4, wherein $R^1$ and $R^2$ taken together are joined to form a cyclopentyl, cyclohexyl or cycloheptyl ring.

6. The sulfamate of claim 1, wherein said sulfamate of formula (I) is selected from the group consisting of:
(2,2-dimethyl-1,3-dioxolan-4-yl)methyl sulfamic acid ester;
(2-methyl-2-nonyl-1,3-dioxolan-4-yl)methyl sulfamic acid ester; or
(1,4-dioxaspiro[4.5]dec-2-yl)methyl sulfamic acid ester.

7. The sulfamate of claim 6, wherein said sulfamate is (2,2-dimethyl-1,3-dioxolan-4-yl)methyl sulfamic acid ester.

8. The sulfamate of claim 6, wherein said sulfamate is (2-methyl-2nonyl-1,3-dioxolan-4-yl)methyl sulfamic acid ester.

9. The sulfamate of claim 6, wherein said sulfamate is (1,4dioxaspiro[4.5]dec-2-yl)methyl sulfamic acid ester.

10. A pharmaceutical composition for the treatment of convulsions comprising an anti-convulsion effective amount of a sulfamate of claim 1 and a pharmaceutically-acceptable carrier.

11. The pharmaceutical composition of claim 10, wherein said sulfamate is present in a unit dosage amount of about 10 to 500 milligrams of the sulfamate.

12. A method for the treatment of convulsions in a mammal which comprises administering to the mammal, an anti-convulsion effective amount of the pharmaceutical composition of claim 10.

13. A chlorosulfate of the following formula (III):

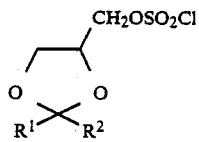 (III)

wherein $R^1$ and $R^2$ are alkyl or taken together are joined to form a cycloalkyl ring.

14. The chlorosulfate of claim 13, wherein $R^1$ and $R^2$ are alkyl of 1 to about 10 carbons or are joined to form a 3 to 7 membered carbocyclic aliphatic ring.

15. An azidosulfate of the following formula (IV)

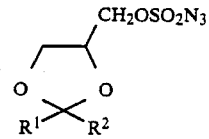 (IV)

wherein $R^1$ and $R^2$ are alkyl or taken together are joined to form a cycloalkyl ring.

16. The azidosulfate of claim 15, wherein $R^1$ and $R^2$ are alkyl of 1 to about 10 carbons or are joined to form a 3 to 7 membered carbocyclic aliphatic ring.

17. The sulfamate of claim 1, wherein $R^1$ and $R^2$ are ethyl.

18. The chlorosulfate of claim 13, wherein $R^1$ and $R^2$ are methyl.

19. The chlorosulfate of claim 13, wherein $R^1$ and $R^2$ are ethyl.

20. The azidosulfate of claim 15, wherein $R^1$ and $R^2$ are methyl.

21. The azidosulfate of claim 15, wherein $R^1$ and $R^2$ are ethyl.

* * * * *